US009964522B2

(12) United States Patent
Udell et al.

(10) Patent No.: US 9,964,522 B2
(45) Date of Patent: May 8, 2018

(54) COMPONENT INSPECTION APPARATUS AND METHOD

(71) Applicant: ALSTOM Technology Ltd, Baden (CH)

(72) Inventors: Christopher Udell, Ennetbaden (CH); Vijayendra Munikoti, Kleinmachnow (DE); Dirk Tscharntke, Berlin (DE); Rémy Schmid, Dachsen (CH); David Thomas Clarke, Warrington (GB)

(73) Assignee: General Electric Technology GmbH, Baden (CH)

( * ) Notice: Subject to any disclaimer, the term of this patent is extended or adjusted under 35 U.S.C. 154(b) by 484 days.

(21) Appl. No.: 14/262,883

(22) Filed: Apr. 28, 2014

(65) Prior Publication Data
US 2014/0318257 A1  Oct. 30, 2014

(30) Foreign Application Priority Data

Apr. 30, 2013  (EP) ..................................... 13165902

(51) Int. Cl.
| G01B 15/00 | (2006.01) |
| G01N 29/265 | (2006.01) |
| G01N 29/22 | (2006.01) |
| G01N 29/26 | (2006.01) |

(52) U.S. Cl.
CPC ......... *G01N 29/265* (2013.01); *G01N 29/225* (2013.01); *G01N 29/262* (2013.01); *G01N 2291/2638* (2013.01); *G01N 2291/2693* (2013.01)

(58) Field of Classification Search
CPC .. G01N 29/265; G01N 29/255; G01N 29/262; G01N 2291/2638; G01N 2291/2693
USPC ........................................................... 73/633
See application file for complete search history.

(56) References Cited

U.S. PATENT DOCUMENTS 6,772,635 B1 * 8/2004 Sale ..................... G01N 29/043
                                                73/622
2005/0126291 A1  6/2005 Czerw et al.
2007/0044564 A1  3/2007 Bui et al.

FOREIGN PATENT DOCUMENTS

| CN | 2687667 Y | 3/2005 |
| CN | 2932390 Y | 8/2007 |
| CN | 101416868 A | 4/2009 |

(Continued)

*Primary Examiner* — John Fitzgerald
*Assistant Examiner* — Rodney T Frank
(74) *Attorney, Agent, or Firm* — GE Global Patent Operation; Cynthia W. Flanigan

(57) ABSTRACT

A component inspection apparatus and a method for ultrasonic inspection of a component, including low pressure last stage steam turbine blades, are disclosed. The apparatus includes a guide member, a guide adapting member and scanning probes. The guide member includes a first surface and a distal second surface. The first surface is configured to adaptably mirror the shape of portions of the component to be inspected. The guide adapting member is capable of releasably attaching the second surface of the guide member. to be changeable as per the shape of the component. The scanning probes may be located on the guide adapting member in a manner configured to be movable along the second surface of the guide member to generate and receive ultrasonic waves used to inspect the component.

11 Claims, 5 Drawing Sheets

(56) References Cited

FOREIGN PATENT DOCUMENTS

EP 2 096 433 9/2009
EP 2 447 714 5/2012

* cited by examiner

0
COMPONENT INSPECTION APPARATUS AND METHOD

CROSS-REFERENCE TO RELATED APPLICATIONS

This application claims priority to European application 13165902.1 filed Apr. 30, 2013, the contents of which are hereby incorporated in its entirety.

TECHNICAL FIELD

The present disclosure relates to a non-destructive material inspection, and, more particularly, to an apparatus and a method for ultrasonic inspection of components, including but not limited to, low pressure last stage steam turbine blades.

BACKGROUND

Non-destructive material inspection using ultrasonic waves for the detection of flaws in components are well known conventionally.

More often than not, challenges arrive while inspecting components, such as aerofoil, filet radius, and specifically, low pressure last stage steam turbine blades using ultrasonic techniques due to varying size, shapes and geometries, and compactness of the components with respect to each other. Generally, for ultrasonic inspection for turbine blades, conventionally known specialized tools are available that have varying shapes and designs and include probes. These conventionally known tools are inserted between the blades for inspection thereof. The probes release and receive ultrasonic waves from the blades to determine flaws in the blades. Among the various requirements for the accurate ultrasonic inspection of the blades by the conventional tool is the essential requirement of matching the tool profile with the blade profile. This requirement makes it essential to produce various tools with probes with respect to each individual blade profile adding to overall cost of inspection of turbine blades.

An example of a known tool is discussed in U.S. patent application no. 2007/0044564 A1. The tool comprises a sensor holder that is shaped to conform to the shape of a test body and further made of a material that enables rapid prototyping. By means of an adjustable corner portion the sensor holder's shape may be adjusted to take into account various widths of the test body along its length. The sensor fixed to the holder may be an ultrasonic inspection device.

Another example of a known tool is discussed in EP2096433A1. The tool comprises a rail for guiding the carriage that is used to hold a test heading configured for nondestructively material testing. The rail is made of, for example, epoxy resin thus enabling quickly manufactured of a rail that conforms to the surface shape of a test body. The rail further includes grooves in which guiding rollers of the carriage can be inserted, that guide the carriage along the length of the rail. This enables the testing head, which is mounted on the carriage, to direct a testing device along a defined path of the test body.

Such conventional tools may be quite in practice, and may have generally been considered satisfactory for their intended purposes, but may be unsatisfactory in terms of adaptability thereof with respect to varying shapes, size and geometries of the blades.

Accordingly, there exists a need for an ultrasonic inspection of components in an economical and adaptable manner.

SUMMARY

The present disclosure describes an apparatus and a method for ultrasonic inspection of a component, such as low pressure last stage turbine blades, that will be presented in the following simplified summary to provide a basic understanding of one or more aspects of the disclosure that are intended to overcome the discussed drawbacks, but not to include all advantages thereof, along with providing some additional advantages. This summary is not an extensive overview of the disclosure. It is intended to neither identify key or critical elements of the disclosure, nor to delineate the scope of the present disclosure. Rather, the sole purpose of this summary is to present some concepts of the disclosure, its aspects and advantages in a simplified form as a prelude to the more detailed description that is presented hereinafter.

An object of the present disclosure is to describe an apparatus and a method, which may be adaptable in terms of being modified for ultrasonic inspection of a component, such as low pressure last stage turbine blades of varying shapes, size and geometries. Another object of the present disclosure is to describe an apparatus and a method, which are convenient to use in an effective and economical way. Various other objects and features of the present disclosure will be apparent from the following detailed description and claims.

The above noted and other objects, in one aspect, may be achieved by an apparatus for ultrasonic inspection of a component. In other aspects, above noted and other objects, may be achieved by a method for ultrasonic inspection of a component. Examples of the components, where such apparatus and method may be utilized, include but is not limited to, low pressure last stage turbine blades, aerofoil and filet radius. While the disclosure will be described in conjunction with the turbine blades for the purpose of better understanding, the scope of the disclosure will extend to all such components where the present apparatus and method may be successfully utilized.

According to the above aspects of the present disclosure, a component inspection apparatus for ultrasonic inspection of a component is disclosed. The apparatus includes a guide member, a guide adapting member and scanning probes. The guide member has a first surface and a distal second surface. The first surface is configured to adaptably mirror a shape of a portion of the component, such that the guide member is adaptably changeable to the shape of a portion of the component while the second surface has a length between distal ends of the surface. The guide adapting member is adapted to be releasably attached to the second surface of the guide member so that during testing the guide adapting member and the guide member do not move relative to each other. The scanning probes are located on the guide adapting member in a manner configured to be movable along the second surface of the guide member and the guide adapting member to generate and receive ultrasonic waves used to inspect the component.

The apparatus may further include a processing unit, which may be utilized to at least visualise and process the ultrasonic waves received by the scanning probes.

In one embodiment of the present disclosure, the guide adapting member may be a flexible steel rail arrangement that is bendably and releasably attachable to the guide member depending upon the shape thereof. In one embodiment, the guide member may be a water-cut mask made from one of a rubber, plastic, wood or metal. In one embodiment, a shape of the second surface of the guide member may be adaptable to a surface shape of a portion of the component to render positioning of the scanning probes to enable the ultrasonic waves to appropriately approach the component. In one form, the scanning probes are positioned such that the ultrasonic waves from the scanning probes approach the component radially to the surface of the component.

In another aspect of the present disclosure, a method for ultrasonic inspection of a component is disclosed. The method includes selecting a guide member as per a shape of a portion of the component to be inspected. The guide member is same as summarized above. The selected guide member from its second surface is releasably attached to a guide adapting member. The guide adapting member is the same as summarized above, and includes scanning probes, similar to that summarized above. Thereafter, the guide member, releasably attached to the guide adapting member, is directed onto a surface of the component, whereat the scanning probes generate and receive ultrasonic waves based on the shape of the component.

The method may further include at least visualizing and processing of the received ultrasonic waves from the scanning probes.

In one embodiment, generating and receiving ultrasonic waves include adapting a shape of the second surface the guide member to a surface shape of a portion of the component to render positioning of the scanning probes to enable the ultrasonic waves to appropriately approach the component. In one form, the ultrasonic waves from the scanning probes may radially approach the component to the surface of the component.

These together with the other aspects of the present disclosure, along with the various features of novelty that characterize the present disclosure, are pointed out with particularity in the present disclosure. For a better understanding of the present disclosure, its operating advantages, and its uses, reference should be made to the accompanying drawings and descriptive matter in which there are illustrated exemplary embodiments of the present disclosure.

BRIEF DESCRIPTION OF THE DRAWINGS

The advantages and features of the present disclosure will be better understood with reference to the following detailed description and claims taken in conjunction with the accompanying drawing, wherein like elements are identified with like symbols, and in which:

Like reference numerals refer to like parts throughout the description of several views of the drawings.

DETAILED DESCRIPTION

For a thorough understanding of the present disclosure, reference is to be made to the following detailed description, including the appended claims, in connection with the above described drawings. In the following description, for purposes of explanation, numerous specific details are set forth in order to provide a thorough understanding of the present disclosure. It will be apparent, however, to one skilled in the art that the present disclosure can be practiced without these specific details. In other instances, structures and apparatuses are shown in block diagrams form only, in order to avoid obscuring the disclosure. Reference in this specification to "one embodiment," "an embodiment," "another embodiment," "various embodiments," means that a particular feature, structure, or characteristic described in connection with the embodiment is included in at least one embodiment of the present disclosure. The appearance of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but may not be of other embodiment's requirement.

Although the following description contains many specifics for the purposes of illustration, anyone skilled in the art will appreciate that many variations and/or alterations to these details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure. Further, the relative terms, such as "first," "second," and the like, herein do not denote any order, elevation or importance, but rather are used to distinguish one element from another. Further, the terms "a" and "an" herein do not denote a limitation of quantity, but rather denote the presence of at least one of the referenced item.

Figure 1:
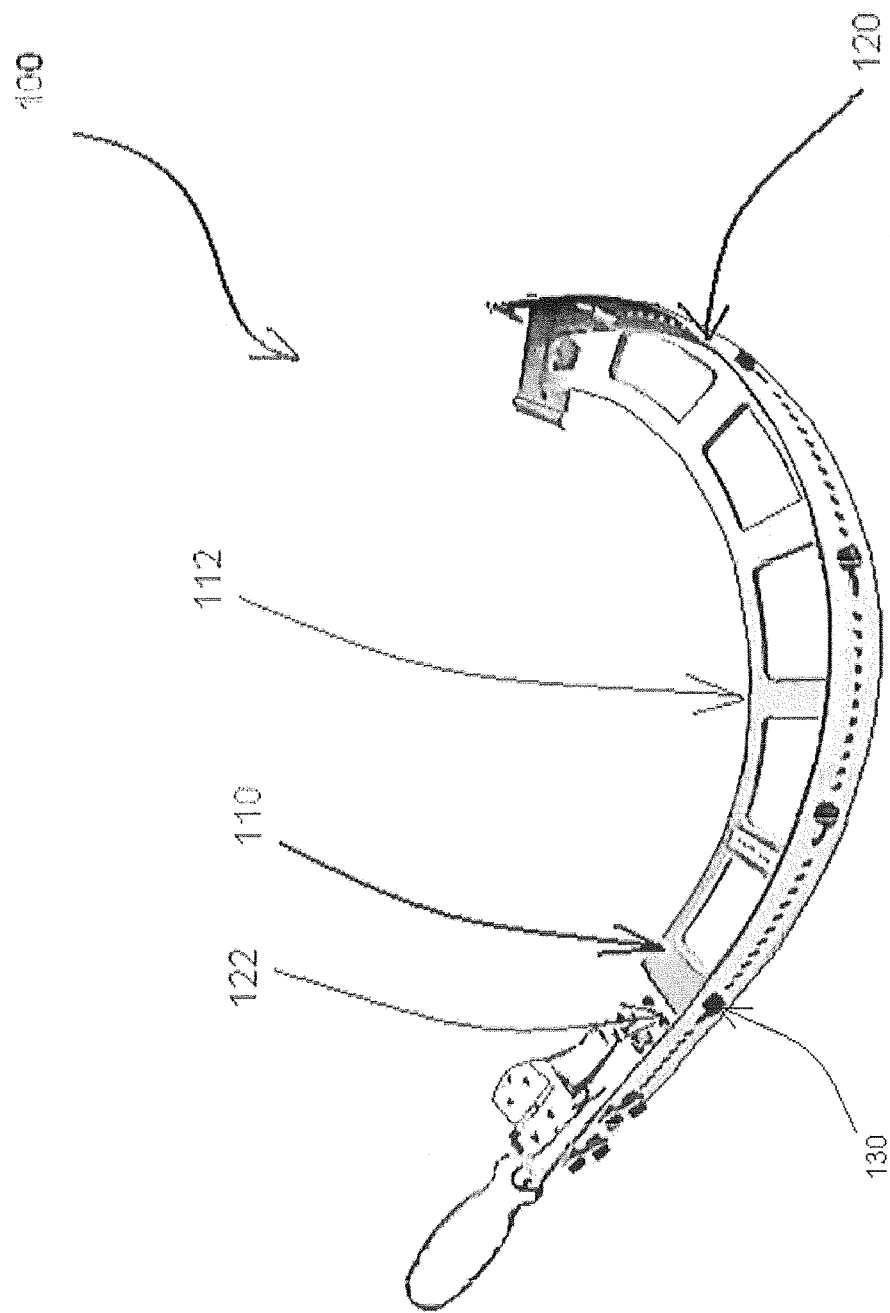
FIG. 1 illustrates an example of an apparatus for ultrasonic inspection of components, in accordance with an exemplary embodiment of the present disclosure.
Figure 2:
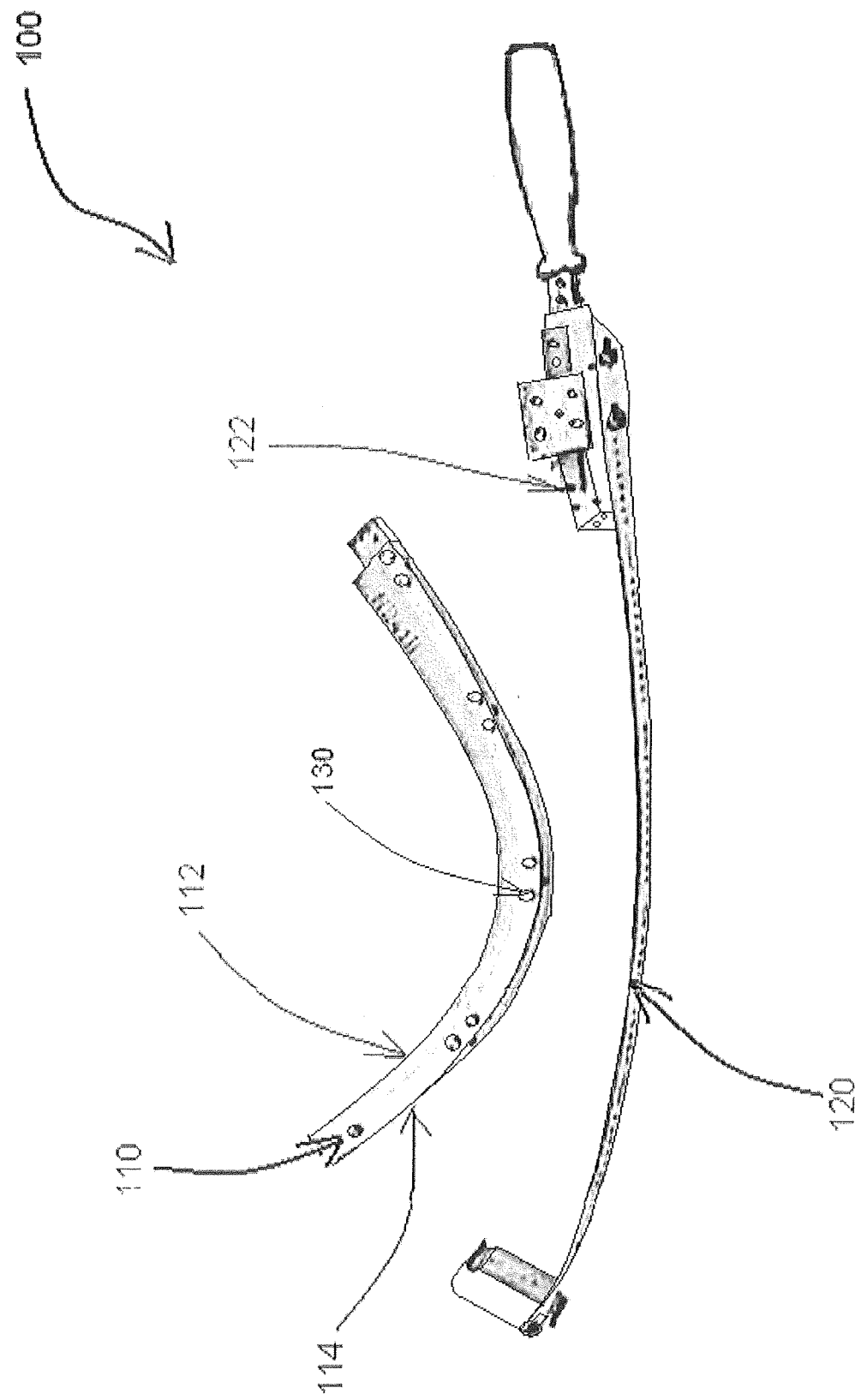
FIG. 2 illustrates an exploded view of the apparatus of FIG. 1, in accordance with an exemplary embodiment of the present disclosure.

Referring now to FIGS. 1 and 2, examples of a component inspection apparatus 100 (hereinafter 'apparatus 100') for an ultrasonic inspection of a component 'C,' (shown in FIGS. 3A and 3B), are illustrated in accordance with an exemplary embodiment of the present disclosure. FIG. 1 illustrates an assembled view whereas FIG. 2 illustrates an exploded view of the apparatus 100. In as much as the construction and arrangement of the apparatus 100, various associated elements may be well-known to those skilled in the art, it is not deemed necessary for purposes of acquiring an understanding of the present disclosure that there be recited herein all of the constructional details and explanation thereof. Rather, it is deemed sufficient to simply note that as shown in FIGS. 1 and 2, in the apparatus 100, only those components are shown that are relevant for the description of various embodiments of the present disclosure.

The apparatus 100 includes a guide member 110, a guide adapting member 120 and scanning probes 122 in a configuration. The guide member 110 includes a first surface 112 and a second surface 114 distal from the first surface 112. Particularly, the first and second surfaces 112, 114 are opposite to each other. The first surface 112 is designed in a manner to adaptably mirror a shape of a portion of the component C to be inspected. The second surface 114 has distal ends with a length therebetween. In one embodiment, the guide member 110 may be a water-cut mask made from one of rubber, plastic or metal. However, without departing from the scope of the present disclosure, the guide member 110 may be made from any other material, such as wood, partial board, etc., by using suitable techniques. Such guide member 110 is configured to the guide adapting member 120. Specifically, the guide adapting member 120 is adapted to be releasably attaching the guide member 110 from the second surface 114 of the guide member 110 by releasable attachments 130 in such a way that during testing the guide adapting member 120 and the guide member 110 do not move relative to each other. This is one a salient feature of the apparatus 100 that the guide member 110 is adaptably changeable as per the shape of the portion of the component C, to be releasably attached over the guide adapting member 120 via the releasable attachments 130. Examples of such releasable attachments 130 may be snap fit attachments, riveted attachments, nut-bolt attachments, and the like.

In one embodiment of the present disclosure, the guide adapting member 120 may be a flexible steel rail arrangement that is bendable so as to adapt a shape of the second surface 114 of the guide member 110 and be releasably attached the guide member 110 independent upon the shape of the guide member 110. That is, the guiding adapting member 120 by being flexible is capable of being releasably attached to guide members 110 of different shapes. Without departing from the scope of the present disclosure, the guide adapting member 120 may be made of any suitable material having required flexibility and bendability to adapt the shape of the second surface 114 of the guide member 110 and to releasably attach the guide member 110.

The scanning probes 122 may be located on the guide adapting member 120 for being configured to be movable along the second surface 114 of the guide member 110 to generate and receive ultrasonic waves used to inspect the component C. In one embodiment of the present disclosure, the scanning probes 122 may be phased array scanning probes, which allow beam steer and skew, i.e. the beam can be steered in two planes. Using such phased array scanning probes, an area or portion which can be inspected from a specific position of the component C may be increased.

In an example, such phased array scanning probes may be moveably positioned along the second surface 114 on the guide member 110, between the guide member 110 and the guide adapting member 120, and may be coupled to a coupler placed proximate to the first surface 112 of the guide member 110 to transmit and receive ultrasonic waves towards and from the second surface 114 for inspection of the portion of the component C. The shape of the second surface 114 of the guide member 110 is adaptable to the surface shape of the portion of the component C to render positioning of the scanning probes 122 to enable the ultrasonic waves to appropriately approach the components C, if required by such coupler. In an example, the scanning probes 122 may be positioned such that the ultrasonic waves from the scanning probes 122 radially approach the component C to the surface of the component C.

The apparatus 100 may include a processing unit for at least visualizing and processing the received ultrasonic waves from the scanning probes 122 for analyzing flaws, such as crakes in the component C.

Figure 3A:
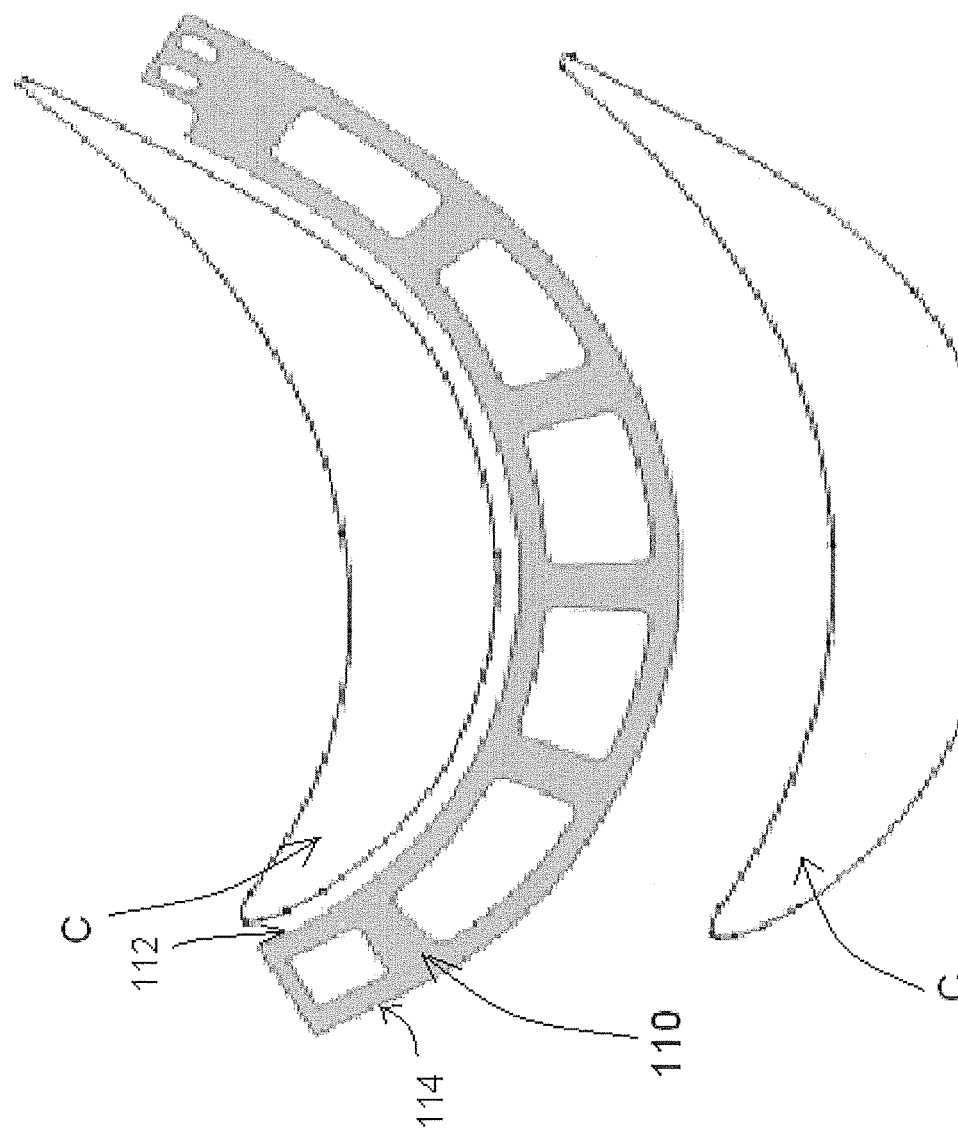
FIGS. 3A and 3B illustrate utilization of the apparatus of FIG. 1 with a component, such as, low pressure last stage turbine blades, in accordance with an exemplary embodiment of the present disclosure.
Figure 3B:
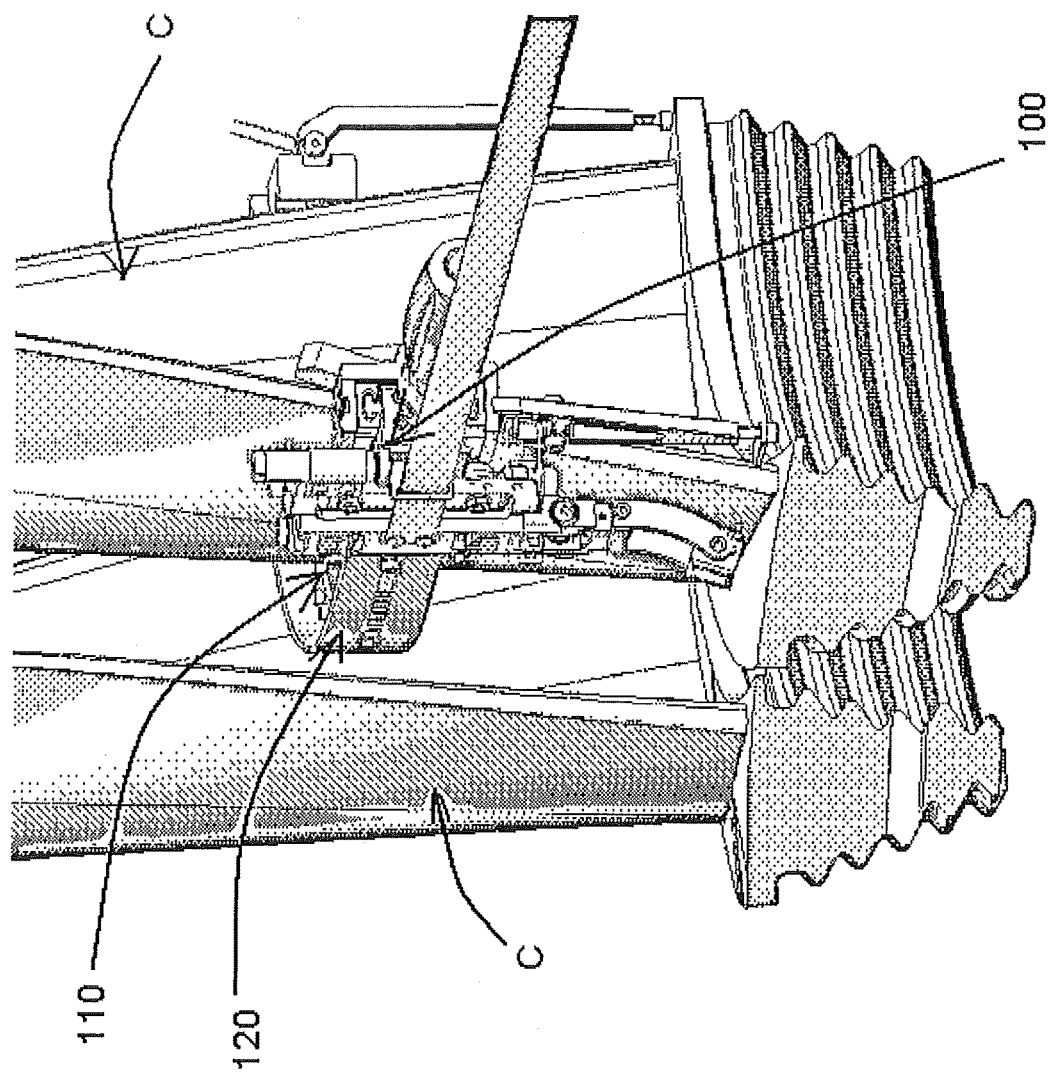

Referring now to FIGS. 3A and 3B, which illustrate ultrasonic inspection of the component C, such as low pressure last stage steam turbine blades, using the apparatus 100. In FIG. 3A, the guide member 110 as per the shape of the portion the component C is selected, and is releasably attached to the guide adapting member 120 by the releasable attachment 130 for configuring the apparatus 100 as shown in FIG. 3B to inspect the component C.

The apparatus 100 may be placed between the turbine blades such that the second surface 114 of the guide member 110 faces that turbine blade which is to be inspected. The guide member 110 is designed, specifically the second surface 114 thereof, to adaptably mirror, i.e. to match the shape of the portion of the turbine blade. Since, the turbine blades are of varying profile, the apparatus 100 may be modified to adapt to any varying size, shape and geometry of the turbine blade to be inspected, by changing the guide member 110 as per the turbine blade profile or the portion of the turbine blade from the guide adapting member 120 to obtain the apparatus, such as the apparatus 100, suitable of a specific turbine blade or a portion of the turbine blade. Upon matching of the profile of the guide member 110 with the turbine blade profile, the scanning probes 122, which is movable along the second surface 114 of the guide member 110 generate and receive ultrasonic waves for scanning the turbine blades. The apparatus 100 may be inserted between the turbine blades even in case of blades mounted inside the turbine, as specifically shown in FIG. 3B.

Figure 4:
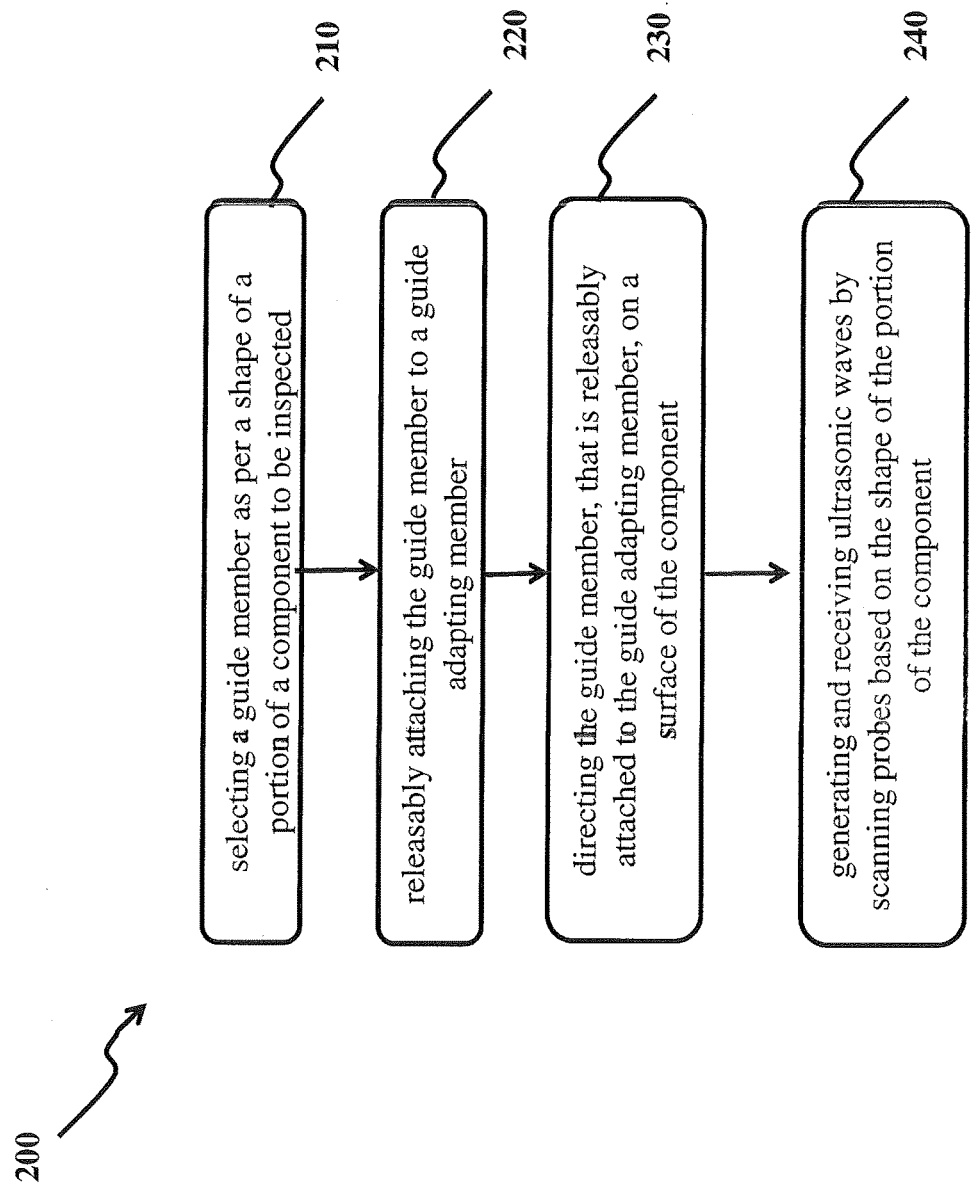
FIG. 4 illustrates a flow diagram depicting a method for ultrasonic inspection utilizing the apparatus of FIG. 1, in accordance with an exemplary embodiment of the present disclosure.

Referring now to FIG. 4, a flow diagram of a method 200 for an ultrasonic inspection of a component C, like low pressure last stage steam turbine blades, is illustrated, in accordance with exemplary embodiment of the present disclosure. The method 200, at 210, includes a selection of a guide member 110, such as the guide member 110, as described above, as per the shape of a portion of the component C. In one embodiment of the present disclosure, selection of the guide member 110 may be made randomly by matching various guide members 110 with the shape of the component C that is to be inspected, to determine a suitable guide member 110 that mirrors the component C. However, without departing from the scope of the present disclosure, the selection of the suitable profile of the guide member 110 as per the shape of the component C may be made by any other technique.

Further, at 220, the selected guide member is releasably attached to a guide adapting member by releasable attachments, such as the releasable attachments 130 as described above. The guide adapting member is same (guide adapting member 120) as described above, and includes scanning probes, similar to the scanning probes 122. Thereafter at 230, the guide member, which is releasably attached to the guide adapting member, is directed on the surface of the component C, and enabling the scanning probes, at 240, to generate and receive ultrasonic waves for inspection of the component C.

The apparatus and the method for an ultrasonic inspection of the components of the present disclosure are advantageous in various scopes. The apparatus and method of the disclosure are adaptable in terms of being modified for ultrasonic inspection of a component, like low pressure last stage steam turbine blades of varying shapes, size and geometries. Specifically, the guide member 110 is changeable per the shape of the component C to be releasably attached over the guide adapting member 120. Further, the apparatus and method are convenient to use and economical. Various other advantages and features of the present disclosure are apparent from the above detailed description and appendage claims.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The embodiments were chosen and described in order to best explain the principles of the present disclosure and its practical application, to thereby enable others skilled in the art to best utilize the present disclosure and various embodiments with various modifications as are suited to the particular use contemplated. It is understood that various omission and substitutions of equivalents are contemplated as circumstance may suggest or render expedient, but such are intended to cover the application or implementation without departing from the spirit or scope of the claims of the present disclosure.

What is claimed is:

1. A component inspection apparatus for ultrasonic inspection of a component, including low pressure last stage steam turbine blades, the component inspection apparatus comprising:
   a guide member having a first surface and a second surface distal from the first surface, wherein the first surface of the guide member is configured to mirror a shape of a portion of the component, such that the guide member is adaptably changeable to the shape of the portion of the component and the second surface of the guide member has a length between distal ends;
   a guide adapting member adapted to be releasably attached to the second surface of the guide member over the length of the second surface of the guide member, such that, during testing, the guide adapting member and the guide member do not move relative to each other; and
   scanning probes located on the guide adapting member in a manner configured to be positioned along the second surface of the guide member to generate and receive ultrasonic waves used to inspect the portion of the component wherein the scanning probe is located in the space between the first surface and the second surface of the guide member.

2. The apparatus as claimed in claim 1 further comprising a processing unit configured and arranged to at least visualise and process the ultrasonic waves received by the scanning probes.

3. The apparatus as claimed in claim 1, wherein the guide adapting member is a flexible steel rail arrangement bendable to adopt a shape of the second surface of the guide member to releasably attach the guide member.

4. The apparatus as claimed in claim 1, wherein a shape of the second surface of the guide member is adaptable to a surface shape of the portion of the component to render positioning of the scanning probes to enable the ultrasonic waves to appropriately approach the portion of the component.

5. The apparatus as claimed in claim 4, wherein the scanning probes are positioned such that the ultrasonic waves from the scanning probes radially approach to the portion of the component.

6. The apparatus as claimed in claim 1, wherein the guide member is a water-cut mask made from one of a selection of rubber, plastic, or metal.

7. A method for ultrasonic inspection of a component, including low pressure last stage steam turbine blades, the method comprising:
   selecting a guide member according to a shape of a portion of the component to be inspected, the guide member having a first surface and a second surface distal from the first surface, wherein the first surface of the guide member is configured to mirror the shape of the portion of the component and the second surface of the guide member has a length between distal ends;
   releasably attaching the guide member to a guide adapting member over the length of the second surface of the guide member, such that, during testing, the guide member and the guide adapting member do not move relative to each other;
   directing the guide member, that is releasably attached to the guide adapting member, onto a surface of the portion of the component; and
   generating and receiving ultrasonic waves by scanning probes, located on the guide adapting member in a manner configured to be positioned along the second surface of the guide member, for inspecting the portion of the component wherein the scanning probe is located in the space between the first surface and the second surface of the guide member.

8. The method as claimed in claim 7, further comprising at least visualizing and processing of the received ultrasonic waves from the scanning probes.

9. The method as claimed in claim 7, wherein the guide adapting member is releasably, flexibly, and bendably attached to the second surface of the guide member.

10. The method as claimed in claim 7, wherein the generating and receiving the ultrasonic waves comprises adapting a shape of the second surface of the guide member to a surface shape of the portion of the component to render positioning of the scanning probes to enable the ultrasonic waves to appropriately approach the portion of the component.

11. The method as claimed in claim 10, including arranging the scanning probes such that the ultrasonic waves from the scanning probes radially approach the surface of the portion of the component.

* * * * *